United States Patent
Knopper et al.

(10) Patent No.: US 8,118,781 B2
(45) Date of Patent: Feb. 21, 2012

(54) FLUID INFUSION SYSTEM, A METHOD OF ASSEMBLING SUCH SYSTEM AND DRUG RESERVOIR FOR USE IN THE SYSTEM

(75) Inventors: Helene Juhldal Knopper, Frederiksberg (DK); Carsten Lund, Vordingborg (DK); Niels Frederik Keiser-Nielsen, Niva (DK)

(73) Assignee: Novo Nordisk A/S, Bagsvaerd (DK)

( * ) Notice: Subject to any disclaimer, the term of this patent is extended or adjusted under 35 U.S.C. 154(b) by 143 days.

(21) Appl. No.: 12/297,339

(22) PCT Filed: Apr. 19, 2007

(86) PCT No.: PCT/EP2007/053866
§ 371 (c)(1),
(2), (4) Date: Feb. 20, 2009

(87) PCT Pub. No.: WO2007/118908
PCT Pub. Date: Oct. 25, 2007

(65) Prior Publication Data
US 2009/0177159 A1    Jul. 9, 2009

Related U.S. Application Data

(60) Provisional application No. 60/796,770, filed on May 2, 2006.

(30) Foreign Application Priority Data

Apr. 19, 2006  (DK) ................ 2006 00539

(51) Int. Cl.
*A61M 1/00* (2006.01)
(52) U.S. Cl. ........................................... 604/151
(58) Field of Classification Search .......... 604/151–156, 604/218, 232, 135, 206; 222/390; 600/431, 600/432
See application file for complete search history.

(56) References Cited

U.S. PATENT DOCUMENTS 1,799,463 A    4/1931    Hein
(Continued)

FOREIGN PATENT DOCUMENTS

CH            265347        11/1949
(Continued)

OTHER PUBLICATIONS

CH 265347 English Translation, published Nov. 30, 1949, CH 265347 previously cited.

(Continued)

*Primary Examiner* — Christopher D Koharski
(74) *Attorney, Agent, or Firm* — Wesley A. Nicolas; Marc A. Began

(57) ABSTRACT

The present application relates to methods and devices for providing a reduced risk of free flow from medical devices such as an infusion pump. A medicament containing reservoir (100) is provided with a piston having a sealing portion (121) formed by a material of a first stiffness. The piston further comprises a core member (110) of a material having a stiffness larger than said first stiffness, the core member comprising one or more connective members (111) being adapted to cooperate with said one or more protrusions of the linear actuation member. The one or more connective members being adapted to be substantially rigid in the axial direction while being resilient in a radial direction, thereby forming a releasable snap or friction fit connection with the linear actuation member. Thereby a mechanism is provided which is engageable by a purely axial relative displacement and which is disengageable by retracting the linear actuation member axially relative to the piston by exerting a pulling force greater than a predetermined limit.

10 Claims, 6 Drawing Sheets

U.S. PATENT DOCUMENTS

| | | | |
|---|---|---|---|
| 3,215,320 A | 11/1965 | Harold et al. | |
| 3,827,602 A | 8/1974 | Nicholls | |
| 3,939,833 A | 2/1976 | Hansson et al. | |
| 4,331,146 A | 5/1982 | Brignola | |
| 4,381,779 A | 5/1983 | Margulies | |
| 4,493,703 A | 1/1985 | Butterfield | |
| 4,498,904 A | 2/1985 | Turner et al. | |
| 4,568,335 A | 2/1986 | Updike et al. | |
| 4,710,170 A | 12/1987 | Haber | |
| 4,973,318 A | 11/1990 | Holm et al. | |
| 4,979,943 A | 12/1990 | Trenner | |
| 5,085,638 A | 2/1992 | Farbstein et al. | |
| 5,094,148 A | 3/1992 | Haber et al. | |
| 5,222,942 A | 6/1993 | Bader | |
| 5,279,585 A | 1/1994 | Balkwill | |
| 5,300,041 A | 4/1994 | Haber | |
| 5,304,152 A | 4/1994 | Sams | |
| 5,331,954 A | 7/1994 | Rex et al. | |
| 5,353,691 A | 10/1994 | Haber et al. | |
| 5,370,628 A | 12/1994 | Allison et al. | |
| 5,411,488 A * | 5/1995 | Pagay et al. | 604/218 |
| 5,462,535 A | 10/1995 | Bonnichsen et al. | |
| 5,496,285 A | 3/1996 | Schumacher et al. | |
| 5,531,693 A | 7/1996 | Vounatsos | |
| 5,591,131 A | 1/1997 | Chen | |
| 5,620,423 A | 4/1997 | Eykmann et al. | |
| 5,626,566 A | 5/1997 | Petersen et al. | |
| 5,688,252 A | 11/1997 | Matsuda et al. | |
| 5,875,976 A | 3/1999 | Nelson et al. | |
| 5,928,202 A | 7/1999 | Linnebjerg | |
| 5,947,929 A * | 9/1999 | Trull | 604/152 |
| 6,004,297 A | 12/1999 | Steenfeldt-Jensen et al. | |
| 6,004,300 A | 12/1999 | Butcher et al. | |
| 6,080,136 A | 6/2000 | Trull et al. | |
| 6,142,978 A | 11/2000 | Niedospial et al. | |
| 6,206,859 B1 | 3/2001 | Niedospial, Jr. et al. | |
| 6,221,046 B1 | 4/2001 | Burroughs et al. | |
| 6,221,053 B1 | 4/2001 | Walters et al. | |
| 6,447,487 B1 | 9/2002 | Cane | |
| 6,569,126 B1 | 5/2003 | Poulsen et al. | |
| 6,800,071 B1 | 10/2004 | McConnell et al. | |
| 2003/0120219 A1 | 6/2003 | Nielsen et al. | |
| 2006/0151545 A1 | 7/2006 | Imhof et al. | |

FOREIGN PATENT DOCUMENTS

| | | |
|---|---|---|
| DE | 1 292787 | 4/1969 |
| DE | 4423753 | 2/1996 |
| EP | 0204977 | 12/1986 |
| EP | 327910 | 8/1989 |
| EP | 497567 A2 | 8/1992 |
| EP | 0395211 | 12/1994 |
| EP | 0893133 | 1/1999 |
| EP | 1002551 | 5/2000 |
| FR | 2003495 | 11/1969 |
| GB | 836279 | 6/1960 |
| GB | 2117249 | 10/1983 |
| JP | 2001-520087 | 10/2001 |
| WO | WO 90/04424 | 5/1990 |
| WO | WO 92/12747 | 1/1992 |
| WO | 92/11049 | 7/1992 |
| WO | WO 97/29798 | 8/1997 |
| WO | WO 98/11927 | 3/1998 |
| WO | WO 99/20330 | 4/1999 |
| WO | WO 02/096487 | 12/2002 |
| WO | WO 03/101368 | 12/2003 |
| WO | WO 2004/014476 | 2/2004 |
| WO | WO 2005/002652 | 1/2005 |
| WO | WO 2007/118907 | 10/2007 |

OTHER PUBLICATIONS

DE 1292787 English Translation, published Apr. 17, 1969, DE 1292787 previously cited.
Final Office Action mailed Oct. 18, 2010 in U.S. Appl. No. 12/297,340, filed Feb. 16, 2009 by Sie et al.
Non-Final Office Action mailed Mar. 19, 2010 in U.S. Appl. No. 12/297,340, filed Feb. 16, 2009 by Sie et al.
Order Dismissing Appeal mailed Mar. 19, 2010 in U.S. Appl. No. 10/308,367, filed Dec. 3, 2002 by Nielsen et al.
Final Office Action mailed Oct. 10, 2008 in U.S. Appl. No. 10/308,367, filed Dec. 3, 2002 by Nielsen et al.
Advisory Action mailed Jul. 23, 2008 in U.S. Appl. No. 10/308,367, filed Dec. 3, 2002 by Nielsen et al.
Final Office Action mailed May 12, 2008 in U.S. Appl. No. 10/308,367, filed Dec. 3, 2002 by Nielsen et al.
Non-Final Office Action mailed Jan. 8, 2008 in U.S. Appl. No. 10/308,367, filed Dec. 3, 2002 by Nielsen et al.
Final Office Action mailed Aug. 6, 2007 in U.S. Appl. No. 10/308,367, filed Dec. 3, 2002 by Nielsen et al.
Non-Final Office Action mailed Apr. 27, 2007 in U.S. Appl. No. 10/308,367, filed Dec. 3, 2002 by Nielsen et al.
Final Office Action mailed Jan. 8, 2007 in U.S. Appl. No. 10/308,367, filed Dec. 3, 2002 by Nielsen et al.
Non-Final Office Action mailed Jul. 7, 2006 in U.S. Appl. No. 10/308,367, filed Dec. 3, 2002 by Nielsen et al.
Non-Final Office Action mailed Sep. 22, 2005 in U.S. Appl. No. 10/308,367, filed Dec. 3, 2002 by Nielsen et al.
Advisory Action mailed Feb. 23, 2005 in U.S. Appl. No. 10/308,367, filed Dec. 3, 2002 by Nielsen et al.
Final Office Action mailed Oct. 20, 2004 in U.S. Appl. No. 10/308,367, filed Dec. 3, 2002 by Nielsen et al.
Non-Final Office Action mailed Mar. 26, 2004 in U.S. Appl. No. 10/308,367, filed Dec. 3. 2002 by Nielsen et al.
Notice of Allowance mailed Jan. 7, 2003 in U.S. Appl. No. 09/111,832, filed Jul. 8, 1998 by Poulsen et al.
Final Office Action mailed Aug. 12, 2002 in U.S. Appl. No. 09/111,832, filed Jul. 8, 1998 by Poulsen et al.
Non-Final Office Action mailed Dec. 14, 2001 in U.S. Appl. No. 09/111,832, filed Jul. 8, 1998 by Poulsen et al.
International Preliminary Examination Report issued in connection with commonly owned PCT Application No. PCT/DK02/00813, mailed Mar. 29, 2004.
International Search Report issued in connection with commonly owned PCT Application No. PCT/EP2007/053865, mailed Jul. 23, 2007.
International Search Report issued in connection with commonly owned PCT Application No. PCT/EP2007/053866, mailed Aug. 9, 2007.
Search Report issued in connection with commonly owned PCT Application No. PCT/DK02/00813, mailed Mar. 25, 2003.
Written Opinion issued in connection with commonly owned PCT Application No. PCT/DK02/00813, mailed Mar. 3, 2004.

* cited by examiner

FLUID INFUSION SYSTEM, A METHOD OF ASSEMBLING SUCH SYSTEM AND DRUG RESERVOIR FOR USE IN THE SYSTEM

CROSS-REFERENCE TO RELATED APPLICATIONS

This application is a 35 U.S.C. §371 national stage application of International Patent Application PCT/EP2007/053866 (published as WO 2007/118908), filed Apr. 19, 2007, which claimed priority of Danish Patent Application PA 2006 00539, filed Apr. 19, 2006; this application further claims priority under 35 U.S.C. §119 of U.S. Provisional Application 60/796,770, filed May 2, 2006.

The present invention relates generally to medical delivery systems for managing medical therapy. More specifically, the invention relates to a medication reservoir for containing a medical fluid and for use in combination with a medical delivery device, wherein the medication reservoir comprises a slideable piston adapted for engaging a linear actuation member of a medical delivery device.

BACKGROUND OF THE INVENTION

In the disclosure of the present invention reference is mostly made to the treatment of diabetes by injection of insulin, however, this is only a preferred use of the present invention.

Diabetes mellitus is the common name for at least 2 different diseases, one characterised by immune system mediated specific pancreatic beta cell destruction (insulin dependent diabetes mellitus (IDDM) or type 1 diabetes), and another characterised by decreased insulin sensitivity (insulin resistance) and/or a functional defect in beta cell function (non-insulin dependent diabetes mellitus (NIDDM) or type 2 diabetes).

The principal treatment of type 1 diabetes is straight forward substitution of the missing insulin secretion, whereas treatment of type 2 is more complicated. More specifically, in early stages of type 2 diabetes treatment a number of different types of drugs can be used, e.g. drugs which increase insulin sensitivity (ciglitazones), decrease hepatic glucose output (e.g. metformin), or reduce glucose uptake from the gut (alfa glucosidase inhibitors), as well as drugs which stimulate beta cell activity (e.g. sulfonylurea/meglitinides). However, the above-described deterioration is reflected in the fact that beta cell stimulators will eventually fail to stimulate the cell, and the patient has to be treated with insulin, either as mono therapy, or in combination with oral medication in order to improve glucose control.

Currently, there are two principal modes of daily insulin therapy, the first mode including syringes and insulin injection pens. These devices are simple to use and are relatively low in cost, but they require a needle stick at each injection, typically 3-4 times or more per day. The second mode is infusion pump therapy, which entails the purchase of a portable but relatively expensive pump, for which reason the initial cost of the pump is a barrier to this type of therapy. Although more complex than syringes and pens, the pump offer the advantages of continuous infusion of insulin, precision in dosing and optionally programmable delivery profiles and user actuated bolus infusions in connections with meals. Further, in combination with a blood glucose sensor an infusion pump may provide fully automatic closed loop control of insulin infusion.

The fluent medicine is usually contained in a reservoir, which can be either a user fillable reservoir or a pre-filled disposable reservoir. Such known reservoir can be provided as a cylindrical barrel having a penetrable membrane at a proximal end and a movable piston at the opposite distal end. A conduit penetrating the membrane is mounted at the proximal end.

When the piston is moved towards the membrane the fluent medicament contained in the reservoir is pressed out through the conduit. When the conduit is mounted it is however possible for the medicament to escape out through the conduit and for the piston to move towards the proximal end only by the influence of gravity. In delivery systems such as pump systems, where the conduit is in contact with the fluid medicament for a substantial period of time, it is normal procedure to connect the plunger to the plunger rod in order to provide a controlled forward movement of the plunger thereby preventing the reservoir from emptying itself.

Some commercially available infusions pumps are adapted to include a user-fillable reservoir, which the user fills with the medicament prior to use. Such fillable reservoirs usually includes a piston having the back wall provided with an interior thread into which a pull rod is screwed. The piston can then be moved backwards inside the fillable reservoir, and the reservoir can be filled with medicine from a vial. Once the reservoir has been filled, the pull rod is disconnected from the piston and the reservoir is inserted into the medication pump.

Depending on the specific design of the pump drive system, a linear actuation member is adapted to engage the piston when a reservoir is inserted into the medication pump. Some coupling mechanisms rely on a positive locking of the linear actuation member to the piston where the coupling is maintained throughout the use of a single reservoir.

Other pump systems may rely on a simple abutment between the linear actuation member and the piston, i.e. the linear actuation member is not positively locked to the piston during pump use. However, in order to take the abovementioned self-emptying into consideration, the friction between the piston and the reservoir wall has to be considered to avoid the risk of free-flow. In commercially available user fillable reservoirs, such as the ones designed for use in insulin pumps marketed by Medtronic Minimed under the trademark PARADIGM, the piston and reservoir are designed such that sufficient friction is established between the piston and the reservoir wall.

Generally, it is desirable to use pre-filled reservoirs in pump systems. However, various conditions have to be taken into consideration in order to provide a reservoir which is suitable for long term storage of insulin. Conventional reservoir materials such as glass for the reservoir wall and specific rubber compositions for completely or partly constituting the piston are generally accepted for constituting insulin prefilled cartridges. Usually, prior to filling, conventional glass cartridges are subject to a siliconization process in order to reduce static friction between the cartridge wall and the piston.

Due to reduced friction compared to the above mentioned user-fillable reservoirs, conventional prefilled glass cartridges cannot be readily adopted in pump systems having a linear actuation member which solely abuts the piston, i.e. does not provide a positive lock, and not at the same time being provided with additional means for excluding free-flow.

Various different references describe mechanisms for ensuring disconnectable but positive locking of a linear actuation member and a piston situated in a reservoir.

However, due to the specific design of the infusion pump, total freedom with respect to the movements required for coupling and uncoupling a linearly moving actuation member and a reservoir comprising a piston is seldom obtainable. These limitations both arise due to the specific movements of the linear actuation member which may comprise axial only or axial as well as rotating movements, and due to the specific movements required when inserting or removing a reservoir into the reservoir receiving section of the infusion pump.

WO patent application No. 2005/002652 discloses an infusion or injection device being provided with a mechanism which secures the connection between a piston and an output member against axial displacement. The connection is established by axially displacing the output member and the piston relative to each other. Disconnection is obtained by relatively twisting the output member with respect to the piston.

According to the various embodiments shown in WO patent application No. 2005/002652, the connection between the actuation member and the piston is provided by a number of resilient engagement parts extending from the actuation member, where the end of the engagement parts cooperates with an internal thread formed in the piston. Due to the piston being formed of a flexible material, and due to the limited contact surface between the piston thread and the engagement parts of the actuation member, a connection is established which is rather flexible in the axial direction, leading to inaccuracies in the amount of fluid dispensed by the infusion pump.

The same deficiencies applies to the connection shown in U.S. Pat. No. 6,447,487 which specifically addresses the problem of free flow. Here a rigid actuation member frictionally engages an inner thread of a rubber piston. Due to the piston being elastically deformable, the engagement between the actuation member and the piston allows for a relative high degree of flexibility along an axis parallel to the dispensing movement.

U.S. Pat. No. 6,800,071 discloses a piston for a fluid medicament reservoir where the piston is formed by a flexible sealing part and a more rigid part inserted in the flexible part, thereby providing rigidity and stability to the flexible part. As discussed in this reference, some pump systems may have an occlusion detection system which uses the axial force on the drive train as an indicator of pressure within a reservoir. The provision of having a relatively stiff and incompressible piston improves the speed that an possible occlusion can be detected. However, the flexible piston part is provided with threads for threadedly coupling the piston to corresponding threads on a linear actuation member of the pump drive system. As the piston threads are formed in the flexible material of the piston, a connection is obtained that may induce some resilience between the piston and the linear actuation member, which again lead to inaccuracies in the amount of fluid expelled from the reservoir, and, the performance of the occlusion detection system is not optimal.

U.S. Pat. No. 5,947,929 discloses a power driven angiographic syringe comprising a driving head adapted to cooperate with resilient hooks formed in the rear of a plunger. Plunger and driving head elements are interactive with a face plate adapter assembly to engage and disengage the plunger and driving head in relation to each other.

In view of the above, it is an object of the present invention to provide a reservoir having an improved piston construction which provides a safe and reliable connection between a linear actuation member of a pump and the piston of the reservoir. Further, it is an object of the invention to provide an improved connection mechanism which ensures a rigid connection between a linear actuation member and the piston where the connection is readably terminated by axially displacing the linear actuation member with respect to the piston.

Further objects and advantages of the present invention will be apparent from the below disclosure as well as from the description of exemplary embodiments.

DISCLOSURE OF THE INVENTION

In the disclosure of the present invention, embodiments will be described which will address one or more of the above objects or which will address objects apparent from the below disclosure as well as from the description of exemplary embodiments.

Correspondingly, in a first aspect a fluid infusion system for infusing a medication fluid which comprises a reservoir adapted to contain the fluid and adapted for use with a pump drive system having a linear actuation member provided with one or more first protrusions. The reservoir comprises a proximal end adapted to connect to an infusion set, an open distal end and a cylindrical wall longitudinally extending along an axis from the proximal end to the distal end. The reservoir further comprises a piston adapted to be slideably mounted within the reservoir along a longitudinal axis and forming a fluid-tight barrier inside the reservoir. The piston comprises at least one peripheral sealing portion made of a material of a first stiffness, and a core member of a material having a stiffness larger than said first stiffness. The core member comprises one or more connective members being adapted to cooperate with the one or more protrusions of the linear actuation member. The one or more connective members are adapted to be substantially rigid in the axial direction while being resilient in a radial direction, thereby forming a releasable connection with the linear actuation member. The connective members and the protrusions of the linear actuation member are so shaped as to mutually engage upon a purely axial relative displacement, to retain said connection upon exertion of an axial disengaging force below a predefined limit acting on the piston away from the actuation member while disengaging the connection when an axial disengaging force exceeds said limit.

The releasable connection may form a frictional engagement or a snapping engagement.

The relevant parts of the system may be designed so that so that the engagement is maintained when an axial disengagement force greater than 1 N is applied, while the engagement is released when an axial disengagement force greater than 10 N is applied to release the engagement by pulling the linear actuation member axially away from the piston.

The linear actuation member may be formed as a male member to cooperate with a female member arranged in the piston core member. Alternatively, the linear actuation member may be formed as a female member to cooperate with a male member arranged in the piston core member.

In a further aspect a method is provided for operating a fluid infusion system suitable for infusing a medication fluid, the method comprising the steps of:
(a): providing a fluid infusion pump comprising a drive system having a linear actuation member provided with one or more protrusions;
(b) providing a reservoir adapted to contain the fluid, the reservoir comprising: a proximal end adapted to connect to an infusion set, an open distal end and a cylindrical reservoir wall longitudinally extending along an axis from the proximal end to the distal end. The reservoir further comprises a piston adapted to be slideably mounted within the reservoir along a longitudinal axis and forming a fluid-tight barrier inside the reservoir, the piston comprising at least one peripheral sealing portion made of a material of a first stiffness, and a core member of a material having a stiffness larger than said first stiffness, the core member comprising one or more connective members being adapted to cooperate with said one or more protrusions of the linear actuation member, said one or more connective members being adapted to be substantially rigid in the axial direction while being resilient in a radial direction, thereby forming a releasable snap or friction fit connection with the linear actuation member;

(c): coupling the reservoir to the infusion pump;

(d): establishing connection between the linear actuation member and the piston by axially displacing said linear actuation member relative to the piston; and (e): releasing the connection between the linear actuation member and the piston by axially displacing said linear actuation member away from the piston.

Said steps (d) and (e) may be performed without relative rotation between the linear actuation member and the piston.

In a yet further aspect a reservoir for use in the above described fluid infusion system is provided.

Further aspects of the invention are disclosed in the appended claims.

The reservoir of all the above described aspects may be formed by a section of glass forming the cylindrical wall. Said wall may on its internal surface be subjected to a siliconizing process. The reservoir may form a pre-filled cartridge with the medicament accommodated therein for forming a unit ready to be used in an infusion pump.

As used herein, the terms "drug, "medicament" and "fluid" are meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the terms "subcutaneous" and "transcutaneous" infusion is meant to encompass any method of transcutaneous delivery to a subject.

BRIEF DESCRIPTION OF THE DRAWINGS

In the following the invention will be further described with references to the drawings, wherein.

DESCRIPTION OF EXEMPLARY EMBODIMENTS

Figure 1:
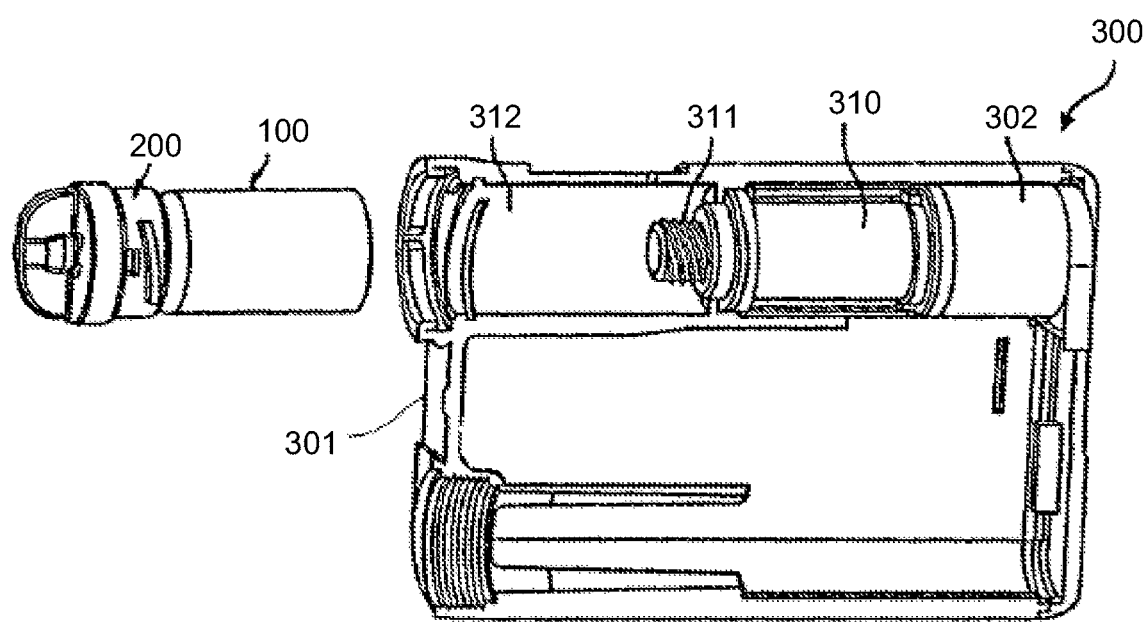
FIG. 1 is a cut-away perspective view of a conventional infusion pump designed for use with the reservoir according to the present invention.

FIG. 1 is a schematic representation of an exemplary infusion pump 300 adapted for receiving a medicament containing reservoir 100 in accordance with the present invention. This schematic representation corresponds to the infusion pump disclosed in U.S. Pat. No. 6,800,071 which is hereby incorporated in its entirety. Infusion pump 300 includes reservoir receiving cavity 312 adapted to accommodate a user-filled or pre-filled insulin reservoir 200.

Reservoir 100 is provided with coupling means for releasably securing a connector 200 to reservoir 100. Connector 200 further forms part of an infusion set which includes an infusion set tubing (not shown). Also, connector 200 comprises coupling means 201 (not shown) for coupling with the housing part 301 of the infusion pump 300, whereby both infusion tubing and the reservoir are coupled to the housing 301 of the infusion pump 300 when connector 200 is secured to the pump housing.

FIG. 1 also schematically depicts a piston drive system comprising a driving device such as a motor 302 arranged for driving a linear actuation member 310 for successively driving a piston accommodated in the reservoir 100 towards the proximal end of the reservoir. In this exemplary embodiment, the linear actuation member 310 is provided with protrusions in the form of an external thread 311, which is adapted for coupling to the piston included in reservoir 100. The remaining parts of the infusion pump are not shown or described here, but are considered the object of a normal design procedure performed by the skilled person along the lines set out in the present specification and in the prior art.

Figure 2:
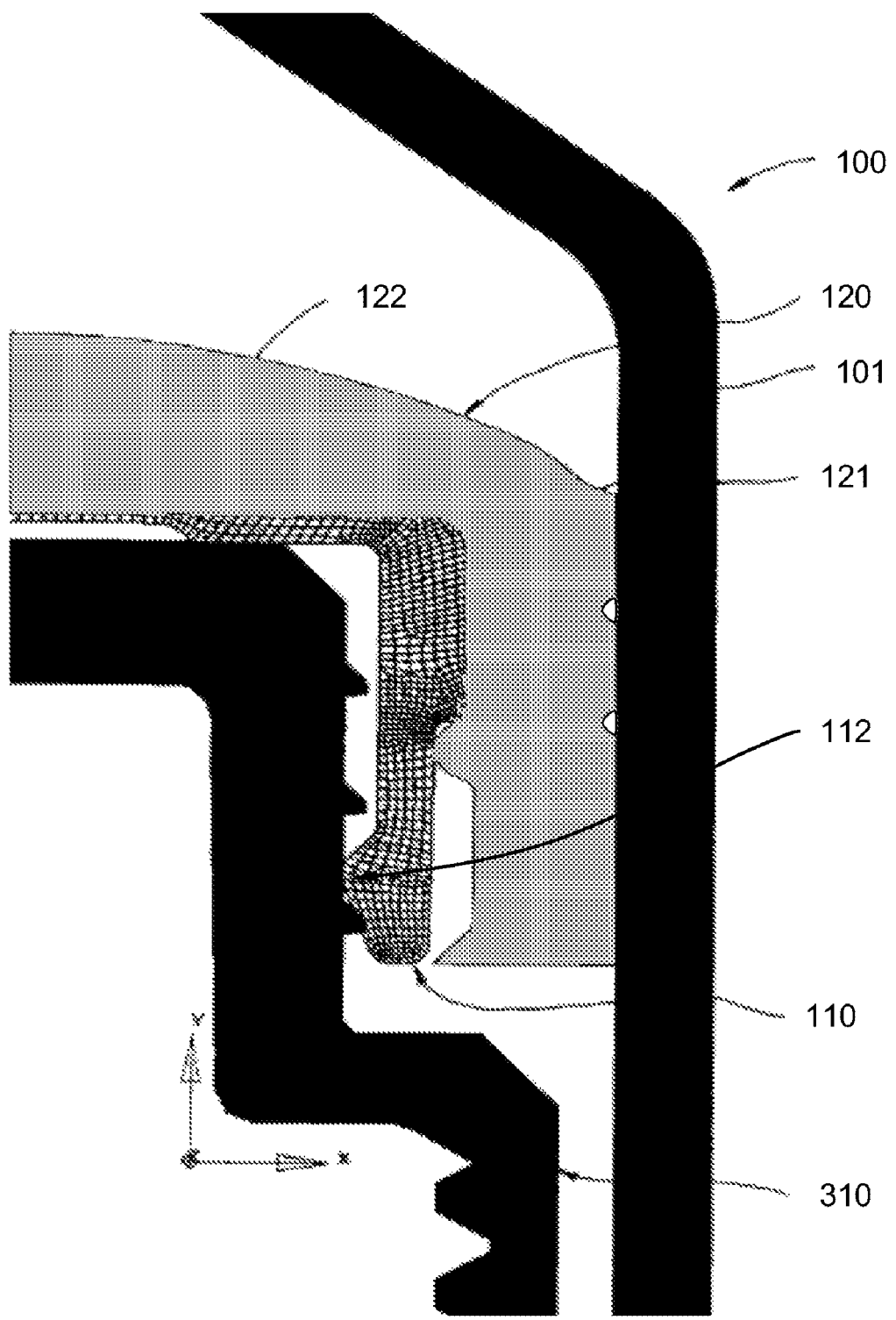
FIG. 2 is a side sectional view of a first embodiment of a reservoir according to the present invention, and a linear actuation member.

Reservoir 100 according to a first embodiment of the invention includes a proximal end closed by a piercable membrane (not shown) and means adapted to connect to an infusion set, an open distal end and a cylindrical wall longitudinally extending between the proximal and the distal end of the reservoir. A section of reservoir 100 is shown in FIG. 2, where 101 denotes the reservoir wall, (110, 120) denotes a piston assembly. Also shown in FIG. 2 is the linear actuation member 310, which is inserted into a cavity of the piston assembly (110, 120). Piston assembly (110, 120) is slideably mounted along the longitudinal axis (indicated by the y-axis) from the distal end of the reservoir towards the proximal end in order to expel medication from the proximal end of the reservoir.

Figure 3A:
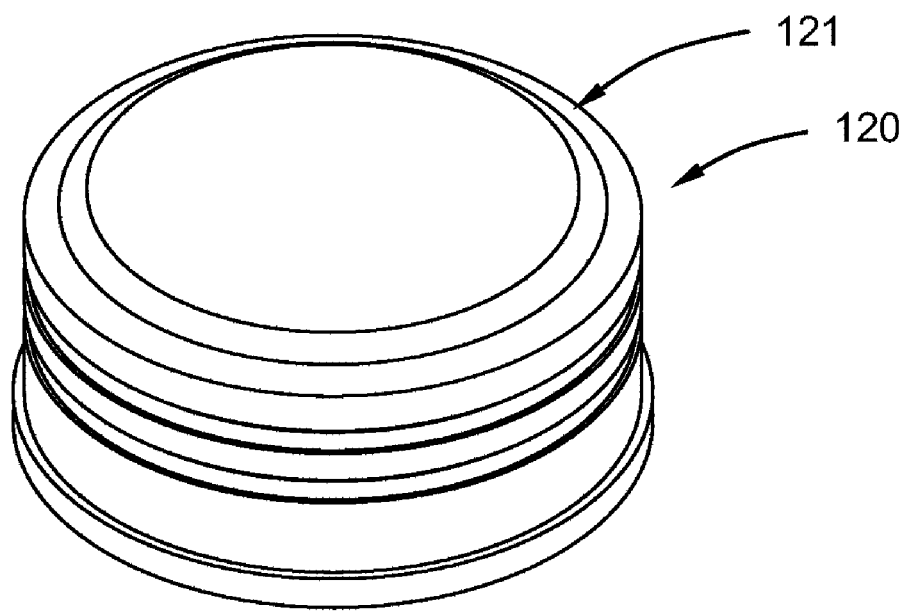
FIGS. 3a and 3b shows perspective views of the proximate side and the distal side respectively of a piston assembly according to the first embodiment of the invention.
Figure 3B:
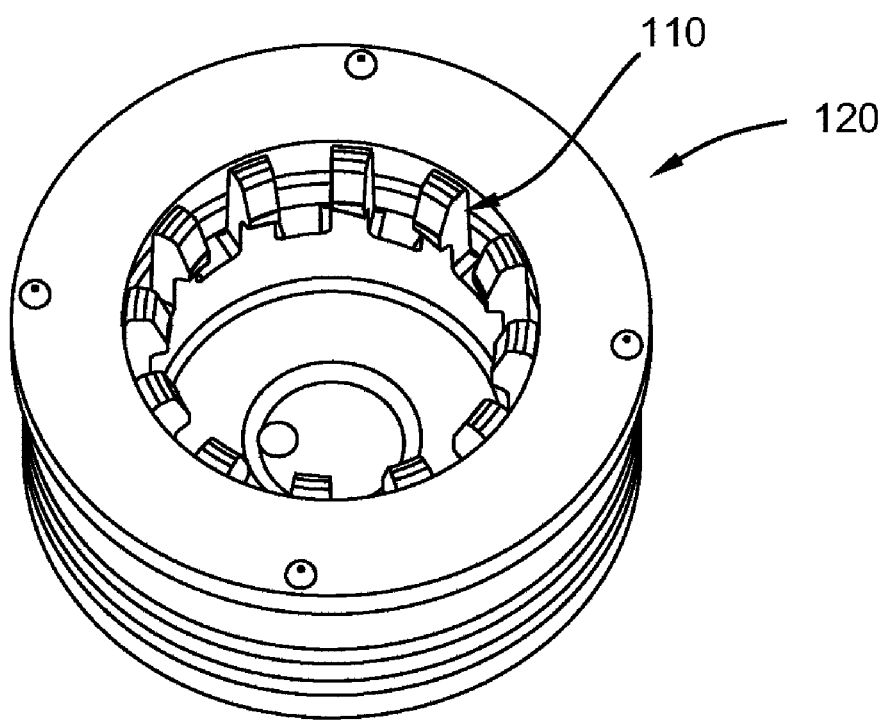

As shown in FIGS. 2, 3a and 3b, the piston assembly comprises a first member 120 made of an elastomeric material such as rubber, and a core member 110 made of a material of greater stiffness than the material of the first member 120. The core member 110 is inserted into a cavity formed in the distal end face of the first member 120. In the embodiment depicted, the first member 120 forms a proximate end face 122 having a generally convex form leading to a peripheral sealing portion 121 along the circumferential wall section 101. Sealing portion 121 and the end face 122 forms a fluid tight barrier. As shown, the first member 120 may include additional sealing rings positioned along the axis of first member 120.

Figure 5:
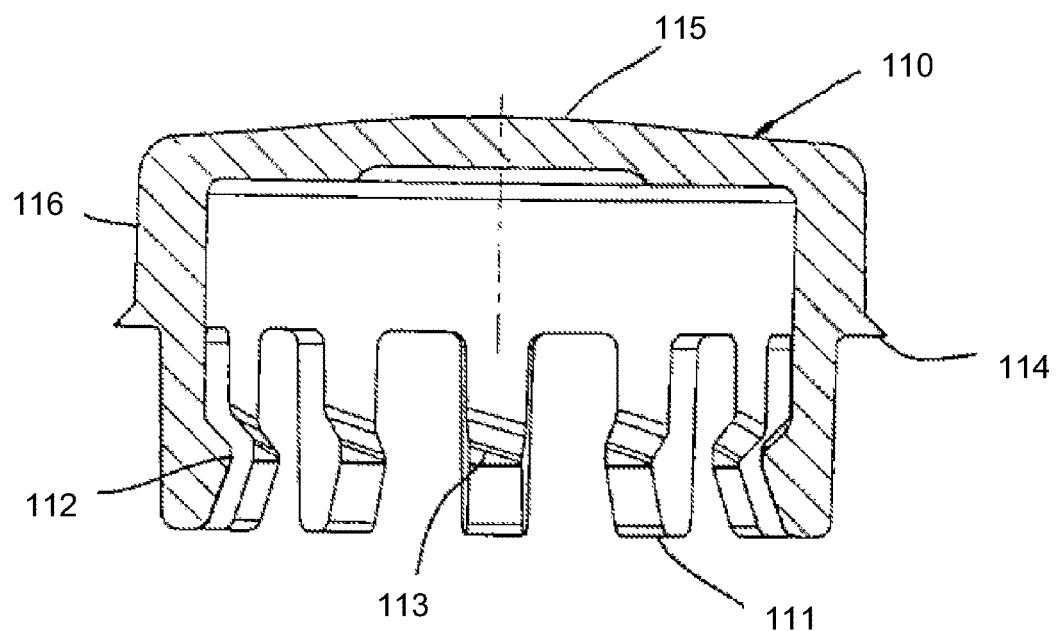
FIG. 5 is a sectional plan view of the core member of the first embodiment, FIG. 6 includes perspective and plan views of a core member of a second embodiment of the invention.

FIG. 5 shows rigid core member 110. Core member 110 generally has a disc or dish-shaped wall section 115 extending in a plane generally perpendicular to the longitudinal axis of the reservoir. In the shown embodiment, core member 110 further comprises a circular ridge 114 extending from the outer circumferential surface of core member 110. When core member 110 is inserted into the cavity of the first member 120, ridge 114 is designed to couple to a circumferential groove 124 formed in the inner surface of said cavity formed in the first member 120 so that core member 110 is fixedly secured to the first member 120. Preferably, the ridge 114 is positioned along the longitudinal direction y of the core member 110 so that the first member 120 is stretched when core member 120 is inserted in first member 120.

The proximate side 115 of core member 110 is generally convex and is so shaped that it stretches the inner proximate end face of the first member 120, when core member 110 is inserted therein. This provision tends to minimize the flexing of the first member 120 if a reduced liquid pressure occurs inside the reservoir, i.e. if the infusion pump is positioned above the needle of an infusion set which is attached to the infusion pump. In general, the first member and the core member are so designed that complete uninterrupted contact is maintained between these two elements during all possible operating conditions.

Figure 4:
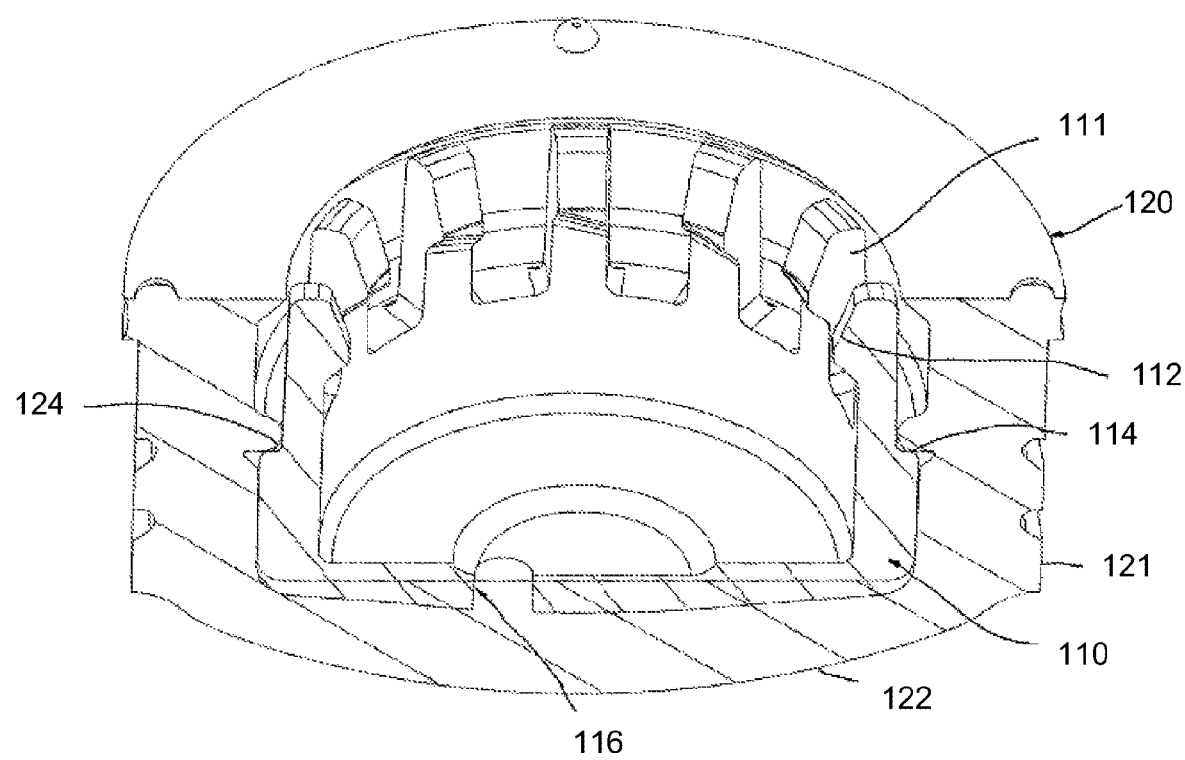
FIG. 4 is a cut-away perspective view of the first embodiment of the invention.

FIG. 4 is a cross sectional view of first member 120 and core member 110. The figure shows the two elements superposed in their unstressed condition and indicates that the proximate wall section of the first member will be stretched when core member 110 is inserted into the cavity formed in the first member 120. Also the side section of the first member 120 will be stressed or expanded in the axial direction by the corresponding side section 116 of core member 110.

Prior to insertion of piston assembly (110, 120) into the cylindrical wall section 101 of the reservoir, the first member 120 is in a generally unstressed condition, allowing core member 110 to be inserted into the cavity formed in first member 120. After the piston assembly has been inserted into the cylindrical wall section 101 of the reservoir, the first member is radially compressed by the wall sections of the reservoir thereby providing a fixed retainment of core member 110 inside first member 120. Due to the form-fitting engagement of core member 110 and the first member 120, and due to the large contact surface between these two elements, a relatively stiff connection is obtained providing minimal flexibility in the longitudinal direction.

Core member 110 further comprises one or more connective members 111 formed as arms extending in the distal direction away from the dish-shaped wall section 115. The one or more connective members 111 generally extends in the longitudinal direction of the reservoir, thereby being substantially rigid in the longitudinal direction. Due to the shape of the connective members 111, the connective members are able to flex in the radial direction. The connective members 111 are adapted to couple with the linear actuation member 310 of an infusion pump, when linear actuation member 310 is inserted into the piston assembly (110, 120).

In the embodiment shown in FIG. 1-5, connective members 111 are formed as 12 shank portion or arms extending in the distal direction, where each arm is provided with a protrusion 112 which are adapted to mate with protrusions formed on linear actuation member 310, i.e. to snap or catch behind protrusions formed on linear actuation member 310. The protrusions 112 may be formed so that a surface part of all or most of the protrusions 112 are in abutment with corresponding surface portions of the protrusions 311 when the linear actuation member is properly seated against the piston rear portion. The said surface portions of the protrusions 311 of the linear actuation member 310 and/or the said surface portions of the protrusions 112 may be inclined with respect to a plane perpendicular to the longitudinal axis to provide a connection disconnectable by axially displacing the piston (110, 120) from the linear actuation member (310).

If the protrusions of linear actuation member 310 are formed as a thread, the connective members 111 may be provided with protrusions 112 arranged in a common plane perpendicular to the longitudinal axis of the reservoir. Further, to ensure line contact between threads of linear actuation member 310 and the protrusions 112, the protrusions 112 may be formed with inclined surfaces portions 113 substantially corresponding to the pitch of the thread of the linear actuation member 310.

Alternatively, the inclined surface portion on each protrusion 112 may be formed symmetrically with respect to each particular connective member 111.

If the protrusions 311 of linear actuation member 310 are formed as one or more circumferential ridges, each of the protrusions 112 may be positioned in mutual different distances from the dish-shaped wall section 115. In this way, it is ensured that at least some of the protrusions 112 catches behind one ridge formed on linear actuation member 310, thereby ensuring a rigid connection having no play.

The number of connective members 111 is generally chosen on the basis of the particular design of the linear actuation member 310 so that at least one connective member is able to engage corresponding protruding elements of the linear actuation member 310. When the protrusions of the linear actuation member 310 forms a thread 311, the number of connective members 111 preferably is in the order of 12-15. Thereby it is ensured that at least one protrusion 112 engages a groove between two consecutive threads 311.

Further, a pure frictional engagement may be obtained. Particularly, this is the case if the linear actuation member 310 is not provided with protrusions. In this case, the connective members 111 are formed to exert a radially inward directed force on linear actuation member 310, the force exerted by the connective members being adapted to grip firmly on the linear actuation member 310.

The core member 110 is preferably formed with a channel or opening 116 extending from the distal side to the proximate side of the core member. Thereby it is ensured that the piston assembly can be properly auto-claved. Also, the first member 120 and the core member 110 are formed so that, during auto-claving, several piston assemblies arranged in a stacked formation cannot stick together and draw vacuum. This can be obtained by ensuring that the connective elements 111 are dimensioned to obstruct the adherence between two consecutive piston assemblies.

Figure 6:
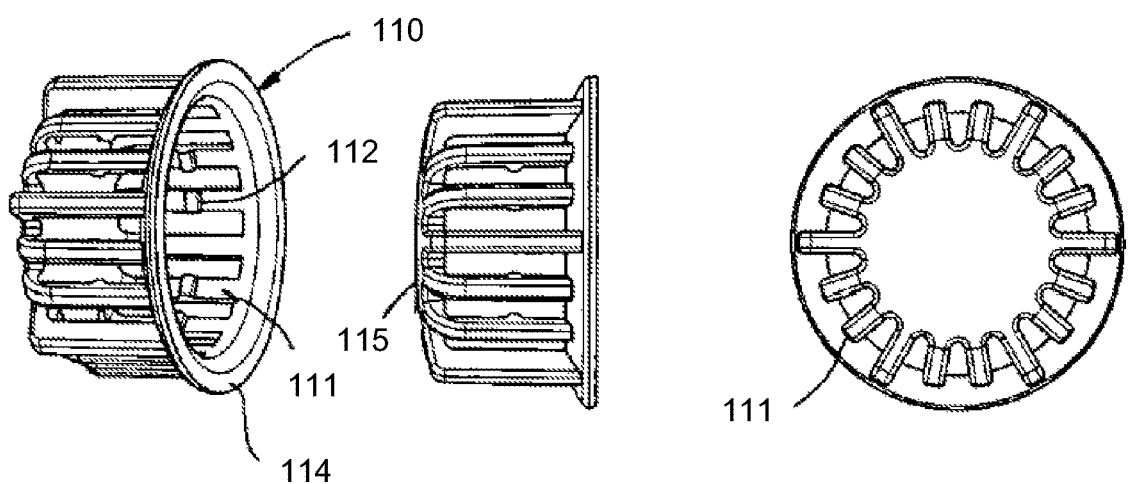
Figure 7:
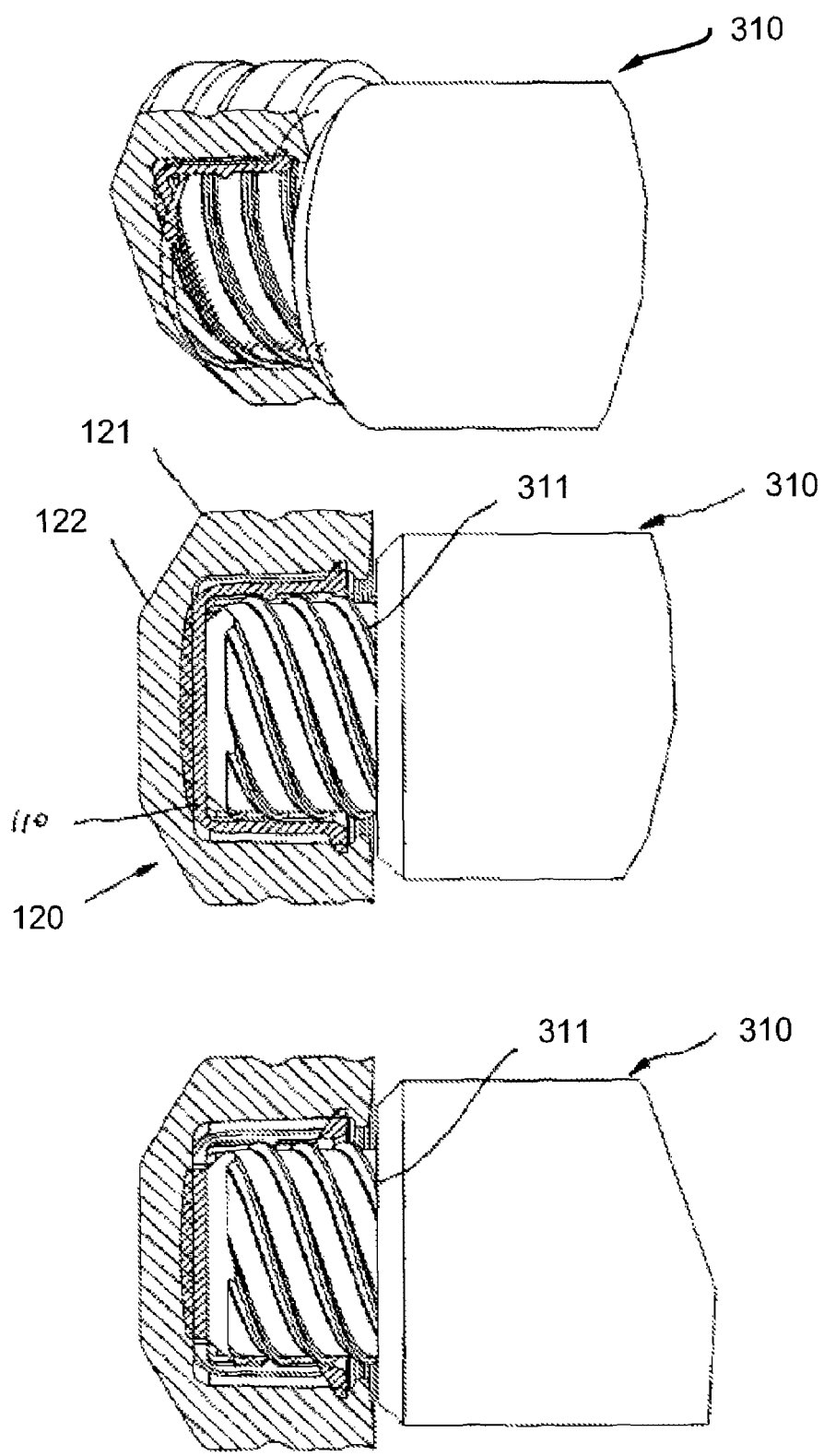
FIG. 7 shows perspective cut-away views of piston assembly of the second embodiment coupled to a linear actuation member.

FIGS. 6 and 7 shows a second embodiment of the invention. The core member 110 in this embodiment generally comprises a dish-shaped proximal wall and a distal rim section including a circular ridge 114. The proximal wall section connects to the distal rim section by a plurality of connective members 111 extending longitudinally along the central axis of the reservoir. Due to the dimensional properties of the connective members 111, each of the connective members are substantially stiff in the longitudinal direction while being able to flex in the radial direction. Again, some or all of the connective members 111 are formed with radially extending protrusions 112 adapted to engage protrusions formed on linear actuation member 310.

In a manner corresponding to the first embodiment, the core member 110 shown on FIG. 6 is adapted to be inserted into a first member 120 which is likewise formed for providing a tight connection between core member 110 and first member 120.

FIG. 7 shows perspective cut-away views of the first member 120 and core member 110 according to the second embodiment. Furthermore FIG. 7 shows a linear actuation member 310. The three elements depicted are shown superposed in their relaxed state as they appear when not mutually connected. Again, it is readily apparent that the first member is expanded by the insertion of core member 110 into the first member 120, thereby obtaining a relatively rigid piston.

In the embodiments shown, the connection between the piston assembly and the linear actuation member 310 may be established as a pure linear axial displacement. However, the connection can also be established where one of the two elements are rotated with respect to the other.

According to the invention, the disconnection between the piston assembly and the linear actuation member 310 may occur by a purely linear axial displacement without jamming the connective elements. Preferably, the connection may be designed to permit disengagement by exerting a linear disengagement force of greater than 1N and less than 10 N. Also, the disconnection may be provided by a relative twisting of the two elements.

In the above described embodiments, the first member 120 and the core member 110 are provided as two distinct members being assembled before insertion of the piston assembly into the reservoir. Alternatively, the core member may be fully or partly molded into the first member by an injection molding operation, whereby the relatively more elastic material forming the first member 120 may be designed to fill out the intervening space between the connective members 111. However, here it is important that the interface between the linear actuation member 310 and the connective members 111 contains little or no elastic material which could reduce the axial stiffness of the connection between the core member 110 and the linear actuation member 310.

The materials chosen for the reservoir wall can be glass or a material made from a cyclic olefin copolymer (COC), or alternatively, polypropylene. The materials for the first member may be any elastomeric material suitable for making a fluid-tight sealing while being compatible for long time storage of the medicament contained in the reservoir. The materials chosen for the core member may fully or at least partially include metal, plastic, COC or polypropylene. If a plastic material is used, the stiffness of the material should be so that the connective members are substantially stiff in the longitudinal direction while being able to flex in the radial direction. Also, in some embodiments, the connective members may be formed partly of metal.

In the above described embodiments, the linear actuation member 310 is formed as a rod for engaging a cavity in the piston assembly (110, 120). Alternatively, the linear actuation member 310 may be formed with a cavity where connective members 111 extending from core member 110 are adapted to be inserted into the cavity of the linear actuation member 310 to provide an engagement interface.

Even though the above described embodiments comprises a first member creating a fluid tight barrier, the piston assembly according to the invention may be formed as a core member in fluid contact with the fluid to be contained inside the reservoir, and wherein the first member are formed as a circumferential seal arranged in a circular channel formed in the circumferential wall of the core member. In this arrangement, the first member may be provided as an o-ring. Also, several distinct sealing members may be arranged at axially different portions of core member. In those further embodiments the fluid tight seal of the piston assembly is obtained by the core member as well as the one or more peripheral seals.

While the above embodiments are based on reservoirs having a cylindrical wall, the invention may just as well apply to reservoirs having polygonal shaped cross section, such as triangular or rectangular shaped cartridges. The reference to circular or radial measures may be adapted to these polygonal shaped embodiments as well, without departing from the scope of the present invention.

In the above description of the exemplary embodiments, the different structures providing the desired relations between the different components just as the means providing the described functionality for the different components of a suitable infusion pump for use in connection with the inventive reservoir have been described to a degree to which the concept of the present invention will be apparent to the skilled reader. The detailed construction and specification for the different structures are considered the object of a normal design procedure performed by the skilled person along the lines set out in the present specification.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A fluid infusion system for infusing a medication fluid comprising:
   a reservoir pre-filled with the medication fluid and adapted for use with a pump drive system having a linear actuation member provided with one or more first protrusions, the reservoir comprising:
      a proximal end closed by a pierceable membrane and adapted to connect to an infusion set;
      an open distal end;
      a cylindrical wall longitudinally extending along an axis from the proximal end to the distal end, and
      a piston adapted to be slideably mounted within the reservoir along a longitudinal axis and forming a fluid-tight barrier inside the reservoir;
      the piston comprising at least one peripheral sealing portion wherein the piston is adapted to engage the linear actuation member by axially displacing the linear actuation member relative to the piston and wherein the engagement is adapted to release when an axial disengagement force exceeds a predefined limit,
   wherein the at least one peripheral sealing portion is made of a material of a first stiffness, and the piston further comprises a core member of a material having a stiffness larger than said first stiffness, the core member comprising one or more connective members being adapted to cooperate with said one or more protrusions of the linear actuation member, and that said one or more connective members are adapted to be substantially rigid in the axial direction while being resilient in a radial direction, thereby forming a releasable connection with the linear actuation member, and
   wherein the connective members and the protrusions being formed to provide a snap fit engagement or a friction fit engagement.

2. The fluid infusion system as defined in claim 1, wherein one or more of the connective members are provided with a second protrusion facing towards a surface portion of the linear actuation member and each of the second protrusions and/or each of the one or more first protrusions is formed with a surface portion engaging the other of the second protrusions and the one or more first protrusions, said surface portions being angled with respect to a plane perpendicular to the longitudinal axis to provide a connection disconnectable by axially displacing the piston from the linear actuation member.

3. The fluid infusion system as defined in claim 1, wherein the one or more connective members are formed as generally longitudinally extending arms, the arms being able to flex radially when coupling or decoupling from the linear actuation member.

4. The fluid infusion system as defined in claim 1, wherein the linear actuation member is provided with one or more threads and that the protrusions of the connective members are formed with inclined surfaces substantially corresponding to the pitch of the thread of the linear actuation member.

5. The fluid infusion system as defined in claim 1 wherein said core member constitutes a piston body, said piston body having a peripheral recessed region for accommodating a peripheral seal.

6. The fluid infusion system as defined claim 1 wherein the piston comprises a piston body made from an elastomeric material, the piston body having an external proximate side being adapted to contact the fluid and an external distal side having an opening leading into a cavity, said cavity adapted to at least partially accommodate the core member.

7. The fluid infusion system as defined in claim 6, wherein the core member has a dish shaped portion arranged perpendicular to the longitudinal axis, said dish shaped portion arranged in intimate contact with an internal proximate wall portion of the cavity formed in the piston body.

8. The fluid infusion system as defined in claim 7, wherein said core member has a generally conical shaped proximal face portion, the conical face portion exerting proximal directed force on said internal proximate wall portion of the piston body when the core member is properly inserted into the piston body.

9. A method for establishing and releasing the connection between a linear actuation member and a piston in a fluid infusion system suitable for infusing a medication fluid, the method comprising:
   providing a fluid infusion pump comprising a drive system having a linear actuation member provided with one or more protrusions;
   providing a reservoir pre-filled with a medication fluid, the reservoir comprising:
      a proximal end closed by a pierceable membrane adapted to connect to an infusion set;
      an open distal end;
      a cylindrical reservoir wall longitudinally extending along an axis from the proximal end to the distal end; and
      a piston adapted to be slideably mounted within the reservoir along a longitudinal axis and forming a fluid-tight barrier inside the reservoir, the piston comprising at least one peripheral sealing portion made of a material of a first stiffness, and a core member of a material having a stiffness larger than said first stiffness, the core member comprising one or more connective members being adapted to cooperate with said one or more protrusions of the linear actuation member, said one or more connective members being adapted to be substantially rigid in the axial direction while being resilient in a radial direction, thereby forming a releasable snap or friction fit connection with the linear actuation member;
   coupling the reservoir to the infusion pump;
   establishing connection between the linear actuation member and the piston by axially displacing said linear actuation member relative to the piston; and
   releasing the connection between the linear actuation member and the piston by axially displacing said linear actuation member away from the piston.

10. A reservoir for use in the fluid infusion system, the reservoir comprising:
   a compartment being pre-filled with a fluid for infusion into the body of a patient and adapted for use with a pump drive system having a linear actuation member provided with one or more protrusions, the reservoir comprising:
   a proximal end closed by a pierceable membrane and adapted to connect to an infusion set;
   an open distal end;
   a cylindrical reservoir wall longitudinally extending along an axis from the proximal end to the distal end;
   a piston adapted to be slideably mounted within the reservoir along a longitudinal axis and forming a fluid-tight barrier inside the reservoir; the piston comprising at least one peripheral sealing portion, wherein the piston is adapted to engage the linear actuation member by axially displacing said linear actuation member relative to the piston and where the engagement is adapted to release when an axial disengagement force exceeds a predefined limit,
   wherein the at least one peripheral sealing portion is made of a material of a first stiffness, and the piston further comprises a core member of a material having a stiffness larger than said first stiffness, the core member comprising one or more connective members being adapted to cooperate with said one or more protrusions of the linear actuation member, and that said one or more connective members are adapted to be substantially rigid in the axial direction while being resilient in a radial direction, thereby forming a releasable connection with the linear actuation member, and
   wherein the connective members and the protrusions being formed to provide a snap fit engagement or a friction fit engagement.

* * * * *